(12) United States Patent
Bronder, Jr.

(10) Patent No.: US 10,010,473 B1
(45) Date of Patent: Jul. 3, 2018

(54) SPINAL DECOMPRESSION HEAD HARNESS AND METHOD OF USE

(71) Applicant: Charles J. Bronder, Jr., Fairfield, NJ (US)

(72) Inventor: Charles J. Bronder, Jr., Fairfield, NJ (US)

( * ) Notice: Subject to any disclaimer, the term of this patent is extended or adjusted under 35 U.S.C. 154(b) by 383 days.

(21) Appl. No.: 14/748,569

(22) Filed: Jun. 24, 2015

Related U.S. Application Data

(60) Provisional application No. 62/018,317, filed on Jun. 27, 2014.

(51) Int. Cl.
| | |
|---|---|
| *A61H 1/00* | (2006.01) |
| *A61H 1/02* | (2006.01) |
| *A61H 23/00* | (2006.01) |
| *A61F 7/00* | (2006.01) |

(52) U.S. Cl.
CPC .............. *A61H 1/0296* (2013.01); *A61F 7/00* (2013.01); *A61H 1/0222* (2013.01); *A61H 1/0229* (2013.01); *A61H 1/0237* (2013.01); *A61H 1/0274* (2013.01); *A61H 23/00* (2013.01); *A61H 2201/0123* (2013.01); *A61H 2201/10* (2013.01)

(58) Field of Classification Search
None
See application file for complete search history.

(56) References Cited

U.S. PATENT DOCUMENTS

| | | |
|---|---|---|
| 2,151,458 A | 2/1938 | Allen |
| 2,574,282 A | 11/1951 | Phillips |
| 2,658,506 A | 11/1953 | Haskell |
| 2,843,114 A | 7/1958 | Hall |
| 3,814,087 A | 6/1974 | Heikes |
| 4,373,523 A | 2/1983 | Treutelaar |

(Continued)

OTHER PUBLICATIONS

Ramos, et al., "Effects of Vertebral Axial Decompression (VAX-D) on Intradiscal Pressure", Journal of Neurosurgery, 81:350-353 (1994).

(Continued)

*Primary Examiner* — Stephen R Crow
(74) *Attorney, Agent, or Firm* — Nixon & Vanderhye P.C.

(57) ABSTRACT

An apparatus for providing sectional (cervical, thoracic and/or lumbar spine as individual parts) and global spinal (full-total spinal: cervical/thoracic/lumbar simultaneous as a single part) decompression including a head harness that has: a rigid member which extends into the mouth cavity of a user; and an attachment point located substantially at the same distance from the center of the skull as the end of the rigid member; wherein the rigid member comprises a U-shaped mouth guard, the u-shaped mouth guard contacting at least the "rear most" upper set of teeth during use; the attachment point is configured to attach to an external force providing apparatus; the attachment point is configured to provide a force in the direction of the user's height via the mouth guard. The location of the attachment point provides an optimal force vector when the device is pulled away from the head in a direction parallel with the user's height for medical applications associated with decompression of the spine. For comfort, positional placement and stability, a forehead pad and cranial straps may be provided.

28 Claims, 11 Drawing Sheets

(56) References Cited

U.S. PATENT DOCUMENTS

| | | | | |
|---|---|---|---|---|
| 4,583,946 | A | * | 4/1986 | Shanel ............... A61C 5/82 |
| | | | | 433/136 |
| 4,890,605 | A | | 1/1990 | Rosendale |
| 4,920,576 | A | * | 5/1990 | Landis ............... A61F 9/02 |
| | | | | 2/10 |
| 5,129,881 | A | * | 7/1992 | Pope ............... A61H 1/008 |
| | | | | 602/32 |
| D415,254 | S | | 10/1999 | Campbell et al. |
| 6,059,548 | A | | 5/2000 | Campbell et al. |
| 6,506,174 | B1 | | 1/2003 | Saunders et al. |
| 7,108,671 | B2 | | 9/2006 | Saunders et al. |
| 9,173,649 | B2 | * | 11/2015 | Clark ............... A61F 5/04 |
| 9,314,272 | B1 | * | 4/2016 | DeMayo ............... A61B 17/66 |

OTHER PUBLICATIONS

Tilaro, Frank, "An Overview of Vertebral Axial Decompression", Canadian Journal of Clinical Medicine, 5(1):1-13 (1996).

Shealy et al., "Emerging Technologies: Preliminary Findings-Decompression, Reduction, and Stabilization of the Lumbar Spine: A Cost-Effective Treatment for Lumbosacral Pain", American Journal of Pain Management, 7(2):63-65 (1997).

Banvissuto, Kimberly, "Non-Surgical Spring Decompression . . . Relief to Patients Suffering from Herniated and Degenerative Disc Disease", M.D. News, Southern Wisconsin Edition, vol. 1:7-8, (2003)http://www.healthworksimc.com/MED_ARTICLE.htm (downloaded from the Internet Aug. 23, 2006).

* cited by examiner

SPINAL DECOMPRESSION HEAD HARNESS AND METHOD OF USE

RELATED APPLICATION

This application claims the benefit of and incorporates by reference U.S. Provisional application 62/018,317, filed on Jun. 27, 2014.

BACKGROUND OF INVENTION

This invention relates to an orthopedic traction type device belonging to the family of devices referred to as head halters or cervical harnesses.

In the field of medical treatment for straightening broken bones or relieving pressure on the spine and skeletal system, traction devices generally are known. Skeletal traction may be used as a technique as part of a treatment therapy to aid with a number of ailments, and spinal compression in particular.

Traction is a common practice involving intermittent and prolonged stretching of: bones, joints, ligaments, spinal cord/nerves, discs, dura mater/thecal sac, fascia and connective tissues in an attempt to relieve symptoms and correct the associated functions of: spinal cord/neural tissues, bones, joints, ligaments, discal pressure/fluid transport gradients, dura mater/thecal sac, fascia and connective tissues. Spinal nerve compression can affect individuals suffering from a large variety of ailments. Traction techniques can aid individuals suffering from arthritis of the spine, disc herniation, disc bulge, degenerative disc disease, facet disease, and a number of other ailments, including general back pain. More specifically, a compressed or pinched nerve can cause at least pain, numbness, weakness, and tingling. Skeletal traction is used to gradually shift spinal abnormalities into their proper alignment and/or to reduce or eliminate compression through the unloading of structures causing compression (bones, disc, and/or other tissues).

Conventional devices that are used such as a neck or head harnesses, e.g., cervical harness, for providing traction often utilize a sling under the chin along with a second sling under the rear portion of the head (skull). In such configurations, the length and amount of distraction/decompression application is quite limited since the straps used in current devices cause stimulation, discomfort, and often pain to the patient due to the distortion/compressive forces arising during application of treatments where the straps contact the skin [and associated structures including the musculature of the head, face, jaw and neck] during use. The straps may cause compression and deformation of the soft tissues and muscles of the face, head, jaw and neck, resulting in strain, fatigue, and pain, often due to muscle spasm. Under such conditions, traction cannot be applied for more than a short period, e.g., fifteen to thirty minutes, before the pain becomes too intense for therapy to continue. Muscle spasms like those described above are counter-productive, since the spasms will prevent the patient from relaxing to the degree necessary for effective treatment.

To provide proper treatment, a physician must avoid unintended stimulation of the structures of the head and neck. Such additional stimulation frequently becomes a trigger which may elicit reflexive cycles of pain, guarding, spasms, etc., and other counter-productive responses.

Current non-invasive, non-pharmaceutical treatment trends and supportive research are investigating many causes of acute and chronic primary/secondary pain generators, including the nerve receptors involved in pain response (mechanoreceptors, nociceptors, etc.). Investigations are likewise being conducted concerning the effects of such pain response, including reflexive mechanisms associated with stimulation and inhibition cycles, as well as resultant immobilization and hypo-mobility.

Any unintended stimulation of the head and neck tissues (direct or indirect) further perpetuates the above discussed cycle. As a result, every attempt is made in medicine to minimize this counterproductive and often harmful effect. The tissues that are part of a joint complex and subject to cell damage and degeneration as a result of potential immobilization and/or hypo-mobility cycles include: skin, subcutaneous tissue, adipose, joint capsules, ligaments, spinal discs, blood vessels, bone, periosteum, muscles, tendons, fascia, aponeuroses, dura mater/thecal sac, epidural tissue, connective tissues, brain/neural tissues and others.

Therapies that promote tissue stretching, elongation, and elasticity function, as well as the unloading/loading, and reduction in pressure gradients, of joints, nerves, discs, connective tissues, cells, and associated structures and systems, e.g., nervous, muscular, skeletal, vascular, have many potential key health benefit applications in the future management of diseases and disorders.

BRIEF SUMMARY OF THE INVENTION

A traction device has been conceived and is disclosed herein for applying a tension force to at least an upper portion of the spine without any compression or compressive forces upon the face, skull, or neck tissues. The traction device includes a head harness including a mouth grip and an overhead connection point for applying a traction force. The overhead connection point and the mouth grip are aligned along an axis of a traction force vector.

To provide a head harness with superior comfort and ease of use, an apparatus has been conceived and is disclosed comprising: an adjustable rigid member, the rigid member comprising an engagement portion and an attachment point; wherein: the engagement portion extends into the mouth cavity of a user; the engagement portion further comprises a force application portion, the force application portion is configured to contact at least the upper set of teeth (inferior surface of the rear maxillary teeth bilaterally) during use; the attachment point is located on the rigid member substantially at the same distance from the center of the skull, relative to a body's mid-line, as the center of pressure applied to the user via the force application portion; the attachment point is configured to attach to an external force providing apparatus; and the attachment point is configured to provide a force in a longitudinal direction via the force application portion.

A method of providing skeletal distraction/traction using a novel apparatus has been conceived and is disclosed comprising: inserting a force application portion attached to an engagement portion of an adjustable rigid member into the mouth of a user, the force application portion being configured to contact at least the upper set of teeth during use; applying a force via at least the force application portion whose vector is directed in a longitudinal direction, the force being adapted to supply tension forces to the user during use; wherein the force is applied via an external force providing apparatus connected via an attachment point on a rigid member, the attachment point being located substantially at the same distance from the center of the skull, relative to a body's mid-line, as the center of pressure applied to the user via the force application portion.

An apparatus for providing skeletal traction has been conceived and is disclosed comprising: a patient supporting surface configured to support a weight of a patient and maintain the patient in a predetermined position; a head harness further comprising an adjustable rigid member, the rigid member comprising an engagement portion and an attachment point; and a force application apparatus; wherein: the engagement portion extends into the mouth cavity of a user; the engagement portion further comprises a force application portion, the force application portion is configured to contact at least the upper set of teeth during use; the attachment point is located on the rigid member substantially at the same distance from the center of the skull, relative to a body's mid-line, as the center of pressure applied to the user via the force application portion; the attachment point is configured to be attached to an external force providing apparatus; and the attachment point is configured to provide a force in a longitudinal direction via the force application portion; and further wherein the attachment point of the head harness is configured to be movably connected to the patient supporting surface in such a way that spinal traction may be applied to a patient during use via the force application apparatus, the force application apparatus being configured to allow a user to apply a force to the head harness such that the force provides decompression to the patient.

An apparatus for providing sectional (cervical, thoracic and/or lumbar spine as individual parts) and global spinal (full-total spinal: cervical/thoracic/lumbar simultaneous as a single part) decompression including a head harness that has: a rigid member which extends into the mouth cavity of a user; and an attachment point located substantially at the same distance from the center of the skull as the end of the rigid member; wherein the rigid member comprises a U-shaped mouth guard, the u-shaped mouth guard contacting at least the "rear most" upper set of teeth during use; the attachment point is configured to attach to an external force providing apparatus; the attachment point is configured to provide a force in the direction of the user's height via the mouth guard. The location of the attachment point provides an optimal force vector when the device is pulled away from the head in a direction parallel with the user's height for medical applications associated with decompression of the spine. For comfort, positional placement and stability, a forehead pad and cranial straps may be provided.

In operation, the apparatus lifts the head solely through the contact of the inferior surfaces of the "rear most—maxillary teeth" (bilaterally) as close to the center of the skull as can be achieved and thus lift cephalic ward with a pure fork-lift type mechanical force. This apparatus device is easily inserted into the face piece portion of a distractive type therapeutic table for the provision of supine, lateral and especially prone cervicothoracic distraction decompression and/or total spinal decompression.

A soft maxillary mouth guard may be used which easily connects/detaches to a rigid plate (metal, etc.) that easily attaches/detaches as an insert into a therapeutic table or the head gear. The mouth guard and rigid plate may be owned by the patient and used for each treatment for the provision of total spinal decompression and prone cervicothoracic traction, distraction, or decompression. Cushions and straps may be provided on the table or head gear for positioning, comfort and stabilization.

DETAILED DESCRIPTION OF THE INVENTION

Figure 1:
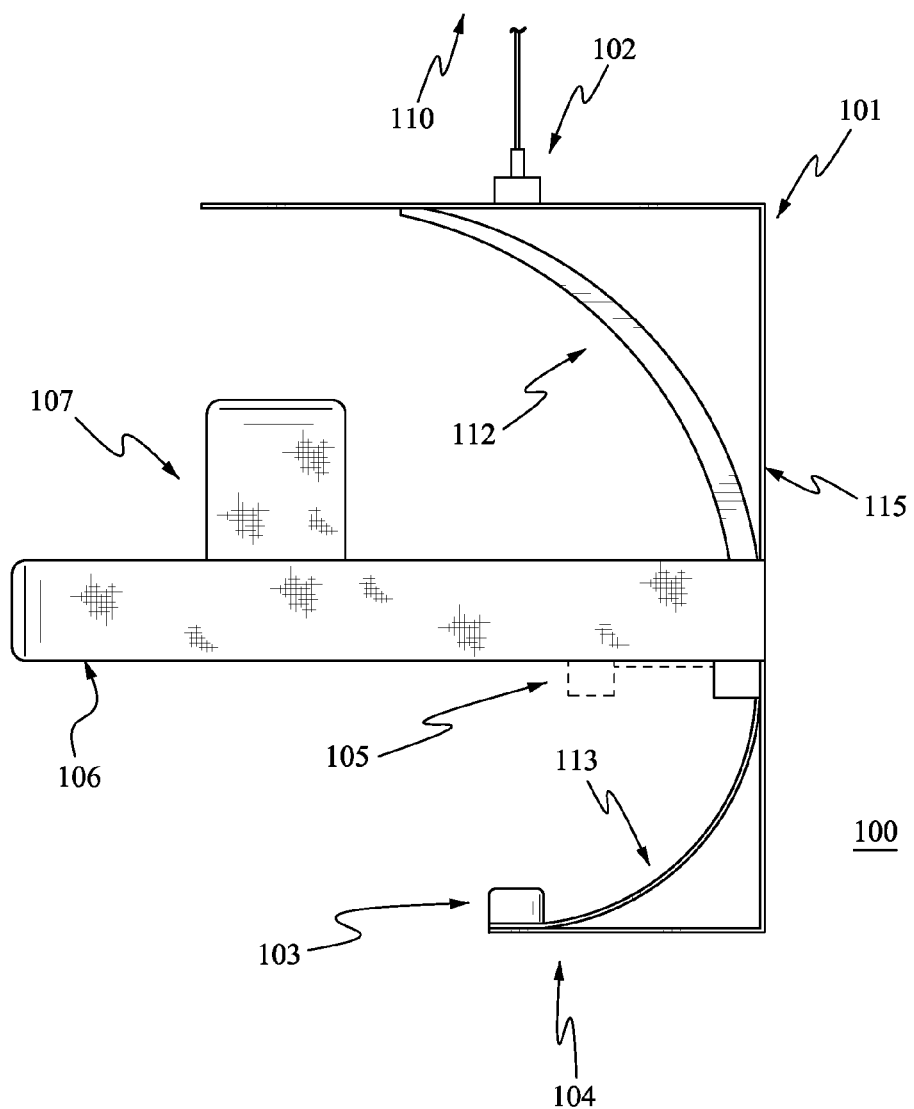
FIG. 1 is a schematic side view of the apparatus.

A simple, easy to use, cost-effective, and comfortable device for applying decompression techniques to a patient during skeletal traction has been conceived and is disclosed here. This device comprises a rigid member providing stability and transmission of an externally applied force to a user through an engagement portion inserted into the mouth, where the force is applied via a force application portion in such a way as to be directed along a vector in the direction of the user's height thanks to the force being applied to the rigid member at a point substantially at the same distance and direction from the body center-line as the contact point with the user in the mouth.

In the past, devices attempting to provide tension forces through head harnesses required the use of straps that extended under the chin, which may cause TMJ and facial tissue pressures, and/or under the occiput, which may cause skull and neck tissue pressures, of the head to transmit any forces applied to the patient. These straps consistently proved to be uncomfortable and made treatment unlikely to succeed due to the externalities associated with pain and discomfort in the patient. Instead, this novel device uses a force application portion, for example, a mouth guard, which transmits the forces applied to the patient through the upper teeth and maxillary facial bones.

The device further recognizes a limitation in previous devices attempting to apply such longitudinal forces as being the location and/or angle at which the forces were applied. This device recognizes and ensures that the application of longitudinal forces will be from an optimal location that lines up closest with the center of pressure applied to the upper teeth by, e.g., the mouth guard.

The device can be utilized anywhere a user can apply a force in the direction of his or her height. For example, the head harness can be configured such that the attachment point is attached to a rope or cable that is directed to a device attached to a wall or hung over a door and allows the user to apply the required force, either manually or through a computer-assisted system.

In an alternate embodiment, the head harness is provided as an attachment to a patient supportive device. The patient supporting device can be, for example, a table capable of supporting the weight of a patient lying supine, prone or side lying. In a variety of non-exhaustive embodiments, such a patient supporting device may have components which abut the patient's shoulders and prevent the patient from sliding along the patient supporting device beyond the shoulder abutting components. In another embodiment, the patient supporting device may have components which interact with a patient's hips, upper thighs, or ankles to provide a stable point from which to pull the patient and provide decompression forces.

In yet another embodiment, the head harness is provided as part of a system providing full spinal decompression, the system applying a first force in the direction of a patient's height via the head harness and additionally applying a second force in a direction opposite the patient's height via an attachment to the lower extremities. In such an embodiment, the second force may be applied via an attachment to the pelvis, calves or ankles of a patient. The second force may be applied cyclically or continuously during a period such as 10 to 30 minutes. This embodiment of applying first and second forces may or may not involve the use of a patient supportive device, such as a therapeutic table, a device to be used while seated, or a device to be used while standing.

FIG. 1 illustrates a schematic side view of one embodiment of the head harness apparatus. A rigid member 101 transmits a force applied via an attachment point 102 through an engagement portion 104 and ultimately a force application portion 103 to a patient using the system. For illustration, the force application portion is a mouth guard in at least one embodiment. Rigid member 101 is composed of a rigid or semi-rigid material capable of receiving a force and transmitting that force without breaking. The rigid member 101, in one embodiment, comprises a top arm 111, a top rib 112, a bottom arm 113, a bottom rib 114, and a backbone 115. The top rib and bottom rib are configured to aid with force application, transmission, and support. The attachment point 102 is provided on the top arm at a position substantially the same distance from the backbone 115 as the mouth guard 103 on the bottom arm 113. This placement of the attachment point provides for an improved vector of force applied to the patient during therapies for decompression. This improved force vector is available because the force vector applied to the attachment point and the force vector applied to the patient via the mouth guard are at substantially the same location relative to the body's midline and therefore line up substantially as one vector in a longitudinal direction.

In addition to the rigid or semi-rigid member, which is adjustable based on patient size, the head harness apparatus features an adjustable forehead pad assembly 105. The forehead pad assembly is connected to the rigid member, but is adjustable vertically (up and down) and laterally (towards and away from the patient) to fit an attached forehead pad 108 to a patient. The pad 108 is configured to provide comfort to a patient during use. As such, the pad itself is configured to be easily laundered, removable, and comfortable when applied to the skin of the forehead. The pad assembly 105 is ideally located approximately at the location or between where top rib 113 and bottom rib 114 converge and attach to backbone 115.

In addition to an adjustable forehead pad assembly with comfortable forehead pad 108, the apparatus also features at least one adjustable head strap 106. The strap may comprise any of the known straps used in a variety of medically viable headgear which are able to provide stability and comfort to a patient. Head straps 106 are configured to encircle the back of the patient's head and provide a counter-force to that force provided by the forehead pad against the patient's forehead. Additionally, the head straps 106 may also optionally comprise an adjustable overhead strap 107, which is connectable to and adjustable relative to the head strap 106. Ideally, such a strap passes over the top of the patient's head approximately at the apogee of the skull. The head strap and cranial strap are adjustable for fit and configured to provide stability to the device. The head strap and overhead strap may utilize hook and loop material.

Figure 2:
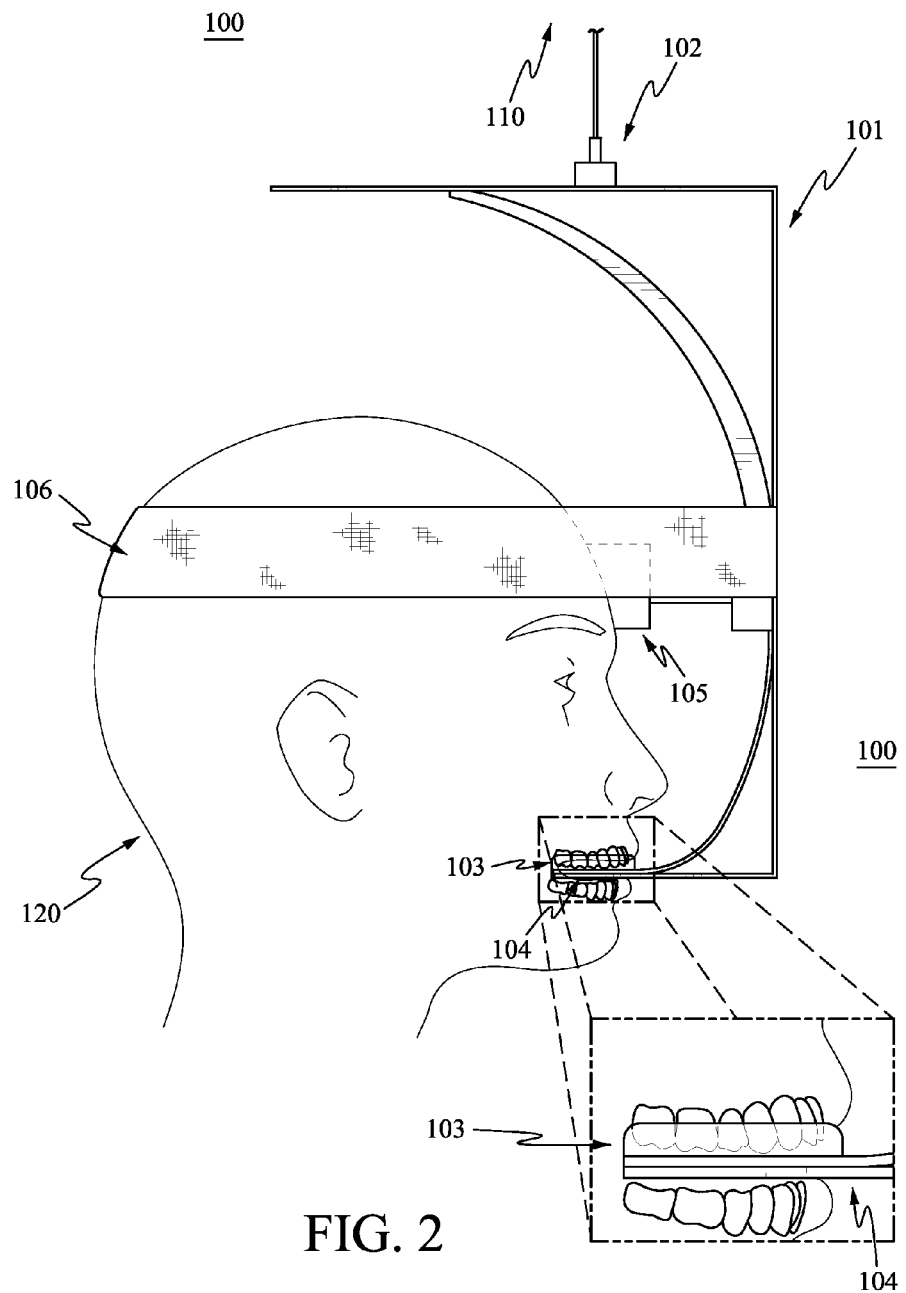
FIG. 2 is an illustration of the apparatus in use in one embodiment.

FIG. 2 is a perspective view of the apparatus in use. A patient 120 positions the mouth guard 103, which is attached at the end of the engagement portion 104, to fit the patient's upper row of teeth. To accomplish this task, the mouth guard may optionally comprise a removable mouth guard piece configured to be molded to a particular patient's upper row of teeth. This molding process may be through the use of a simple rubberized mouth guard which may be softened using hot water, or through a more permanent process by which a mold of the patient's teeth is taken and used to fabricate a personalized permanently molded mouth guard. Optionally, the mouth guard 103 may be a simple universal mouth guard configured to engage the upper teeth of the patient.

In the alternative, the mouth guard 103 may be a double-sided mouth guard that is configured to engage both the top and bottom rows of teeth. Such a configuration as an alternate embodiment permits additional comfort for a patient and permits the patient to bite down if desired to enhance the connection between the patient and the device.

Figure 3:
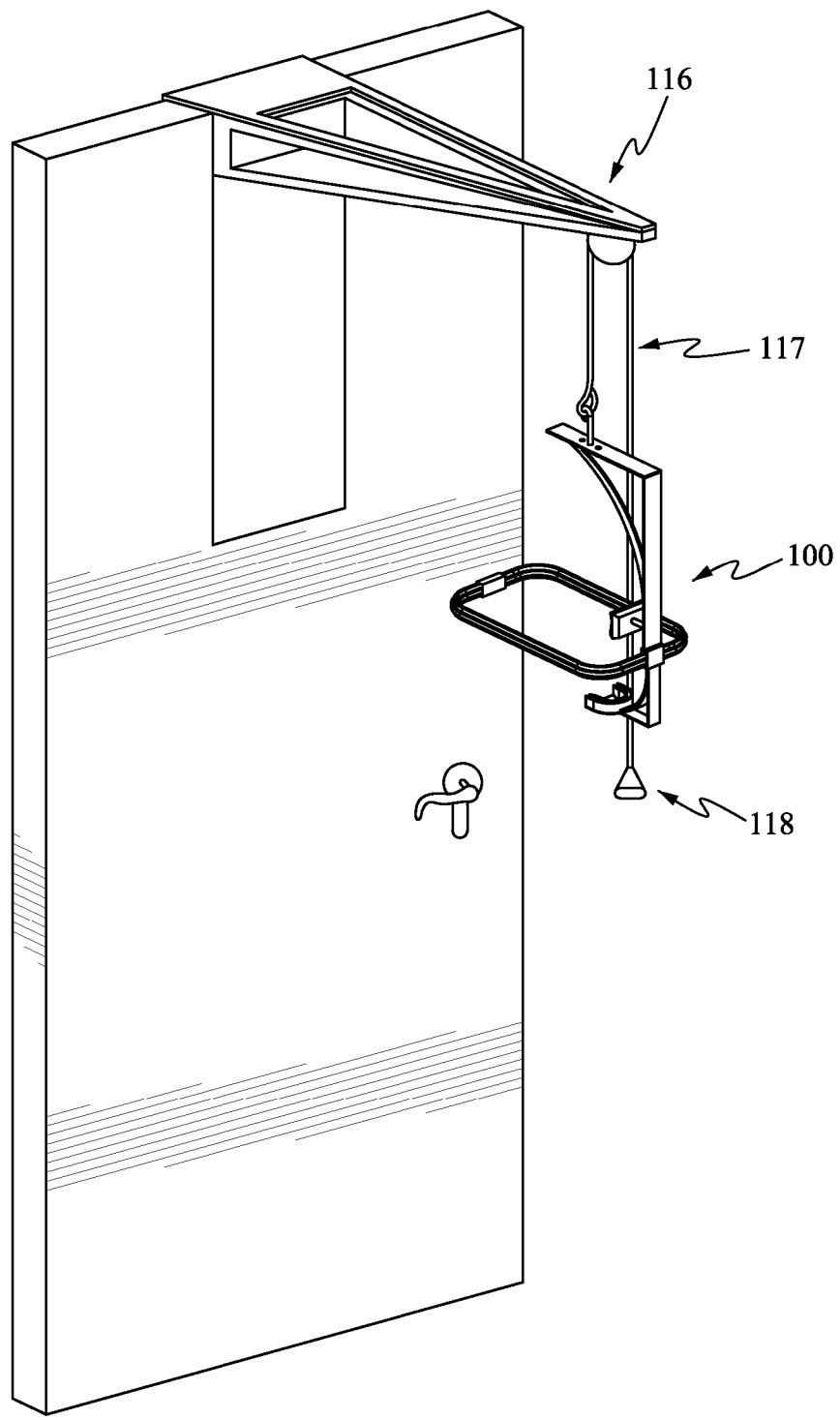
FIG. 3 is an illustration of the apparatus in an alternate embodiment featuring an over-the-door apparatus for home use.

FIG. 3. is an illustration of the apparatus in an alternate embodiment featuring, e.g., an over-the-door apparatus for home use. In this alternate embodiment, a patient may attach an overhead apparatus to a door, a wall, or a number of conventional devices configured to provide vertical resistance. In this illustration, overhead apparatus 116 is an over-the-door apparatus featuring a cable 117 and a hand grip 118. In a variation of this alternate embodiment, the hand grip 118 may be replaced with an automated system utilizing a controller to operate a program designed to provide tension.

Figure 4:
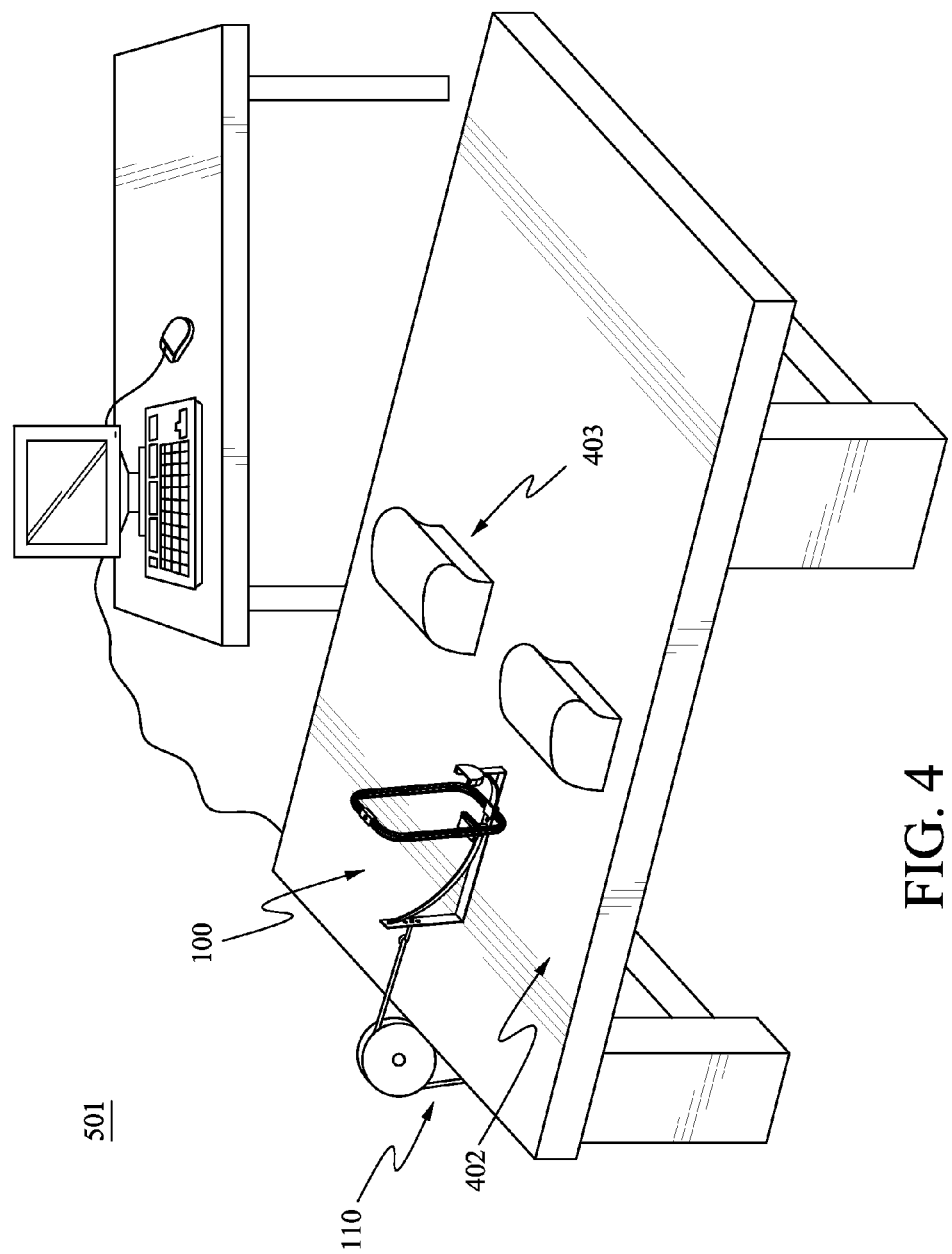
FIG. 4 is an illustration of the apparatus in an alternate embodiment featuring a table upon which a patient may lie down in a supine or prone position and which also features an upper body immobilization component which abuts the patient's shoulders.

FIG. 4 is an illustration of the apparatus in an alternate embodiment featuring a table upon which a patient may lie down in a supine or prone position and which also features an upper body immobilization component which abuts the patient's shoulders. In this alternative embodiment, a patient lies down upon a table 401 comprising a patient supporting surface 402 which is configured to support the weight of the patient as well as provide comfort during therapy. The patient supporting surface may be configured to additionally provide heat, massage, vibration, cold, or other therapies. In one embodiment, the table further comprises an upper body immobilization component 403. The upper body immobilization component is configured to prevent movement of the patient's body in the direction of the applied tension force. Without such a component, the tension force would drag the body and fail to provide adequate decompression. In this illustration, the upper body immobilization component is featured as a set of pads which abut the patient's shoulders on their superior side to provide resistance to movement. Such a configuration is best for cervical spinal decompression. Alternate embodiments may comprise chest or other harnesses configured to accomplish the same immobility.

Figure 5:
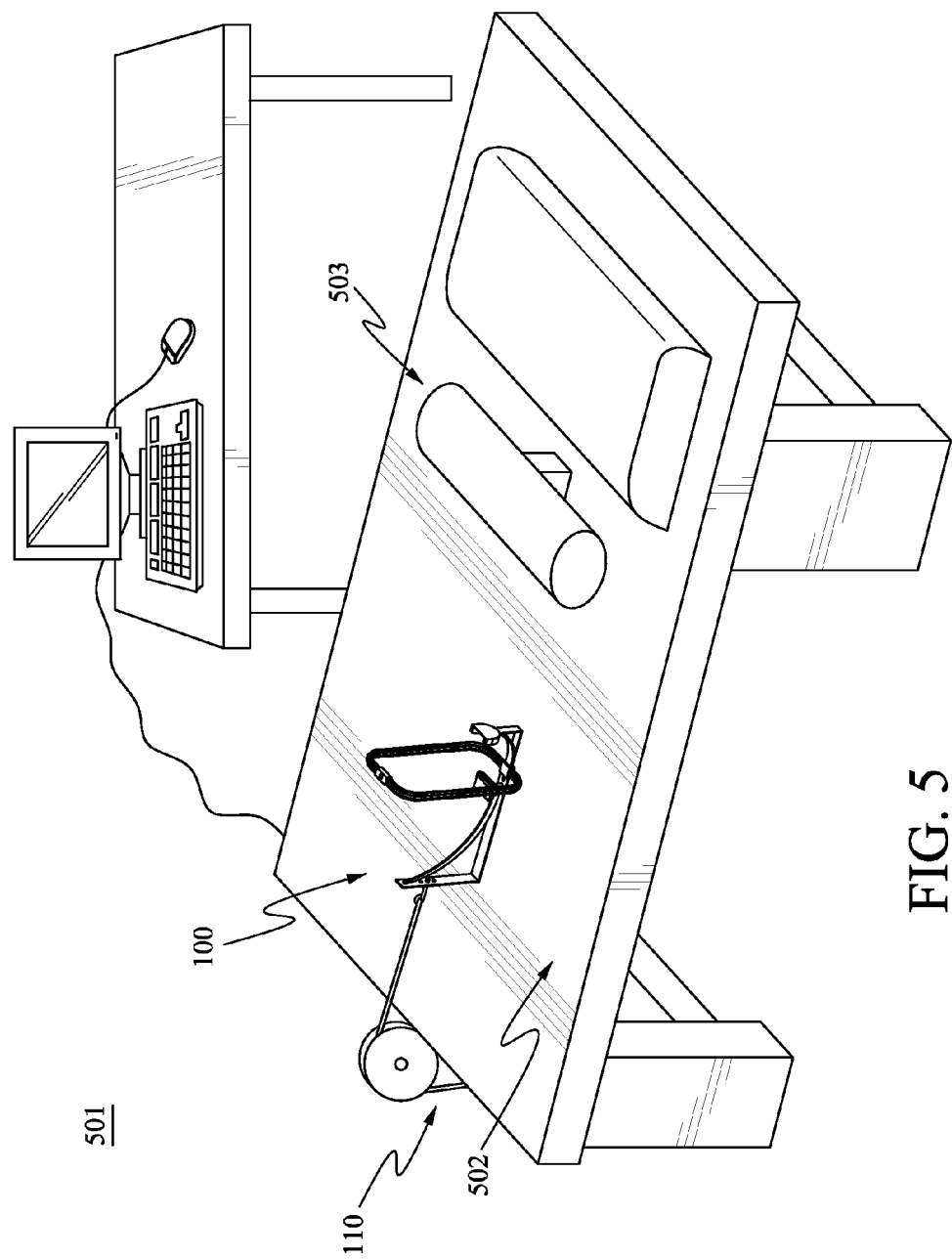
FIG. 5 is an illustration of the apparatus in an alternate embodiment featuring a table upon which a patient may lie down in a supine or prone position and which also features a lower body immobilization component which abuts the patient's legs.

FIG. 5 is an illustration of the apparatus in an alternate embodiment featuring a table upon which a patient may lie down in a supine position and which also features a lower body immobilization component which abuts the patient's legs. In this alternative embodiment, a patient lies down upon a table 501 comprising a patient supporting surface 502 which is configured to support the weight of the patient as well as provide comfort during therapy. The patient supporting surface may be configured to additionally provide heat, massage, vibration, cold, or other therapies. In one embodiment, the table further comprises a lower body immobilization component 503. The lower body immobilization component is configured to prevent movement of the patient's body in the direction of the applied tension force. Without such a component, the tension force would drag the body and fail to provide adequate decompression. In this illustration, the lower body immobilization component is featured as a set of pads which abut the patient's upper legs on their anterior and posterior sides to provide resistance to movement. Such a configuration is best for lumbar and thoracic spinal decompression. Alternate embodiments may comprise hip, leg, ankle, or other harnesses configured to accomplish the same immobility.

Figure 6:
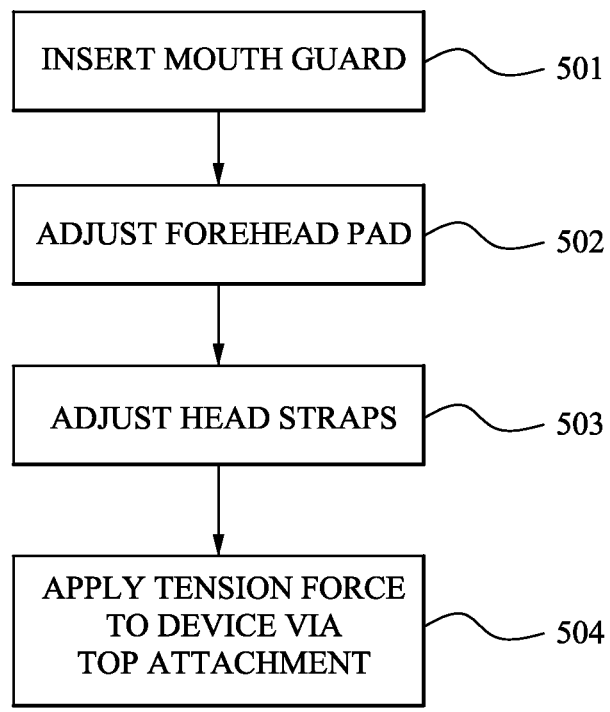
FIG. 6 shows generally a flowchart describing the method of use of the apparatus.
Figure 7A:
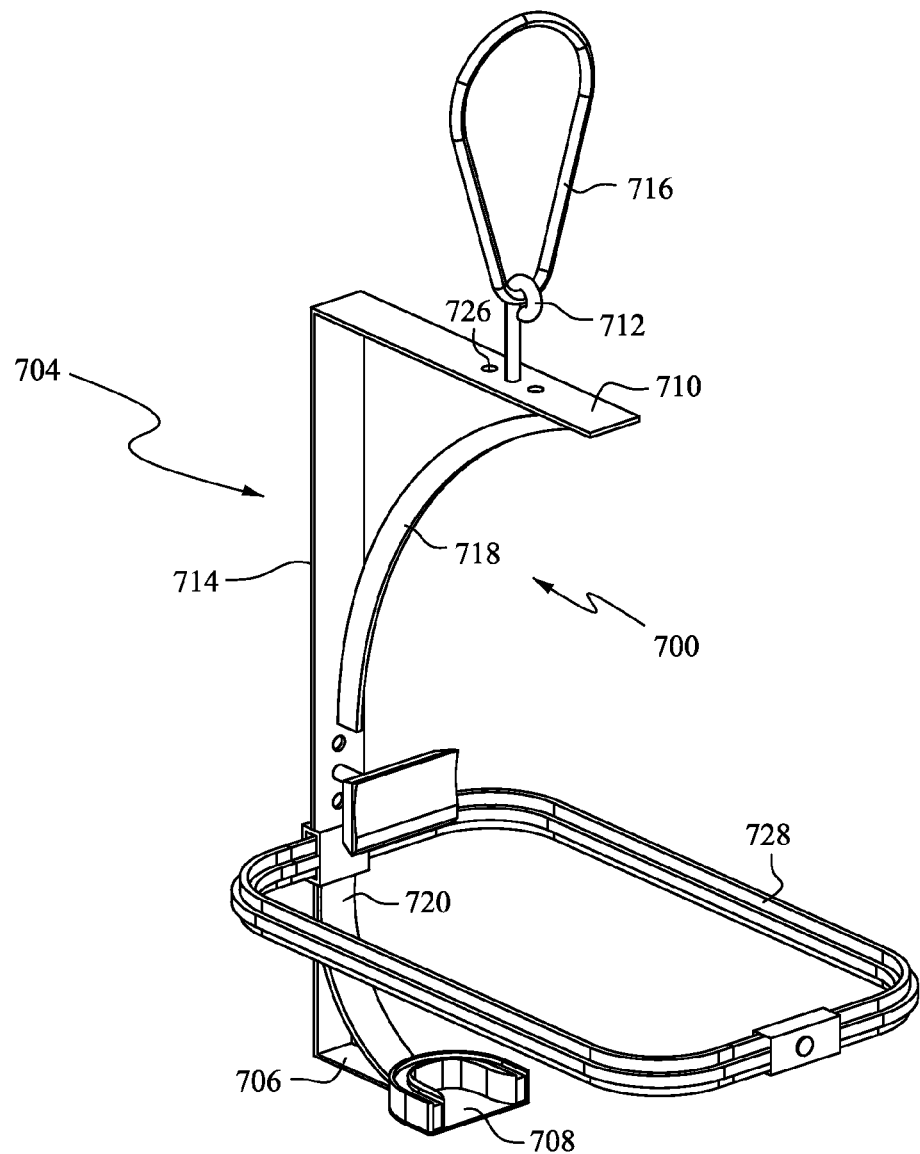
FIG. 7(a) to (e) are illustrations showing various views of an embodiment of the apparatus.
Figure 7B:
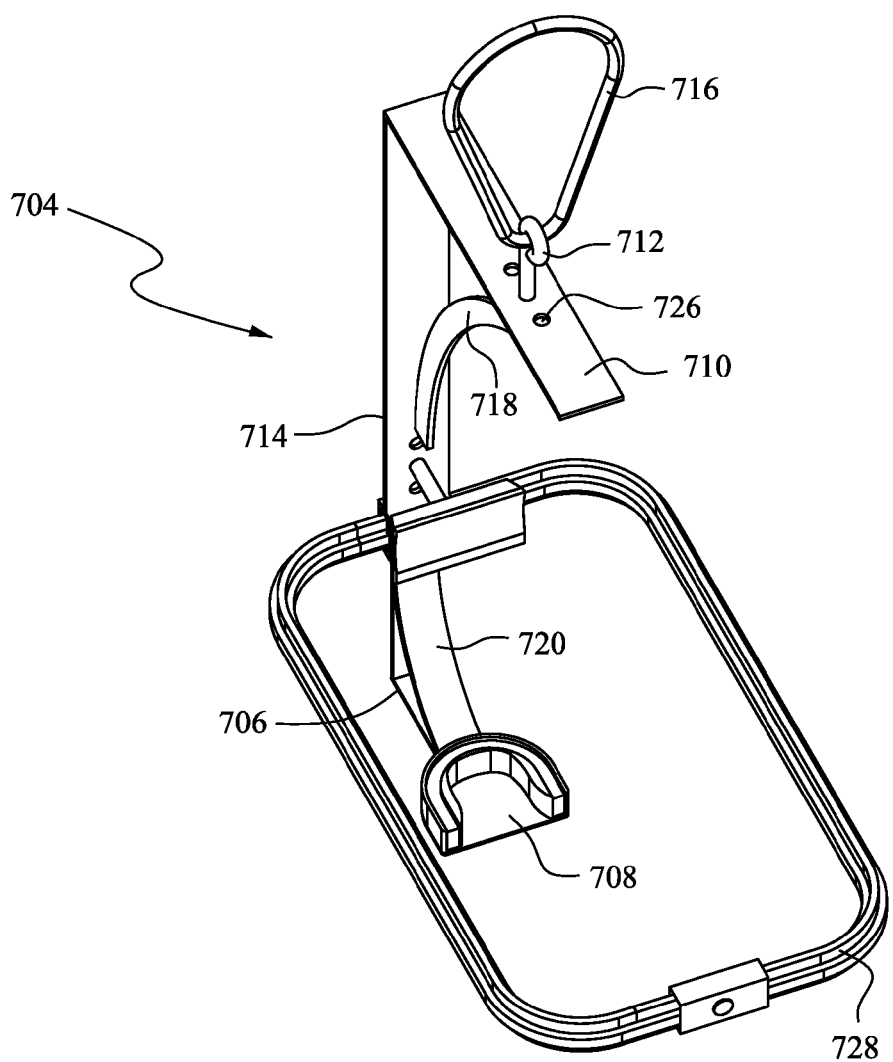
Figure 7C:
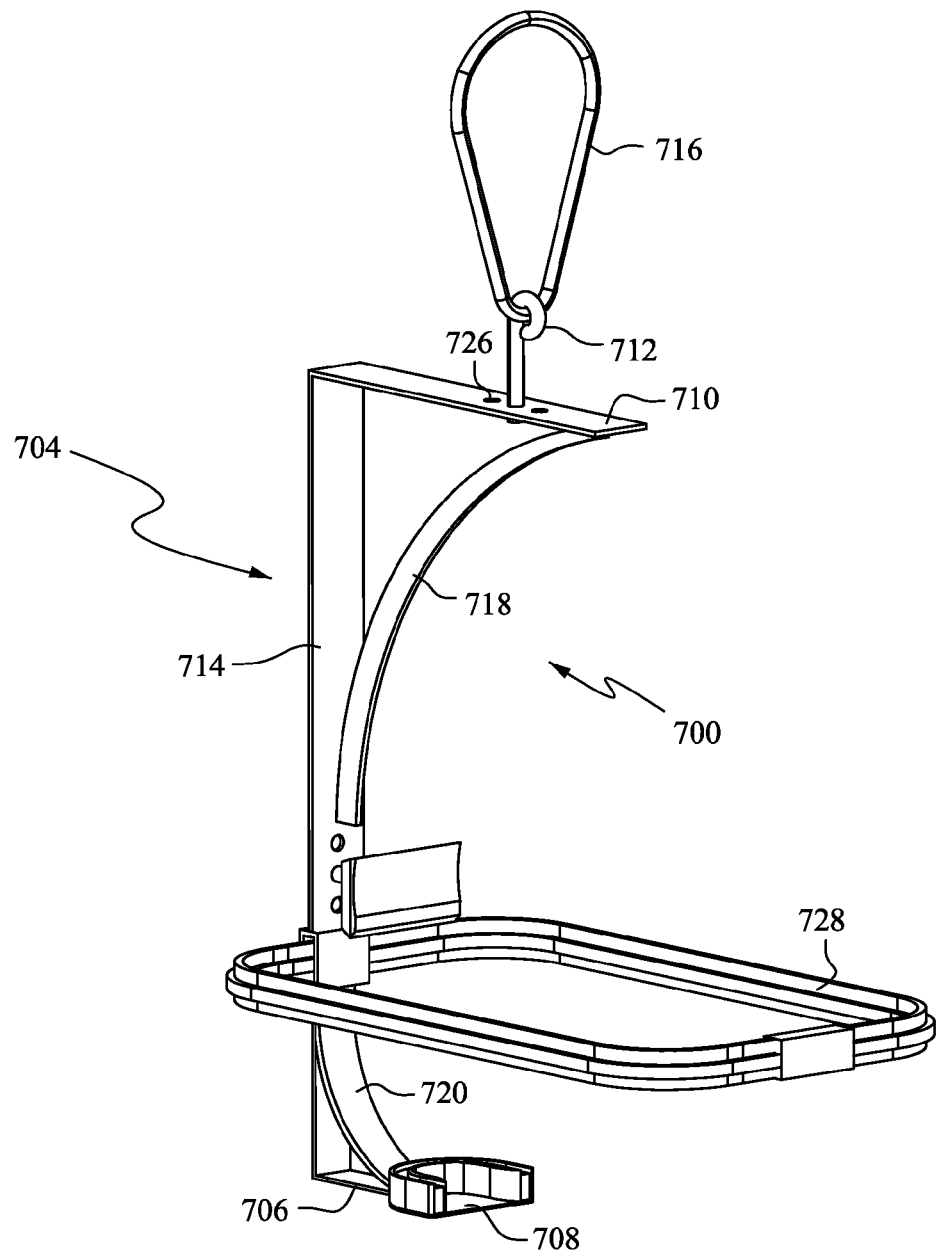
Figure 7D:
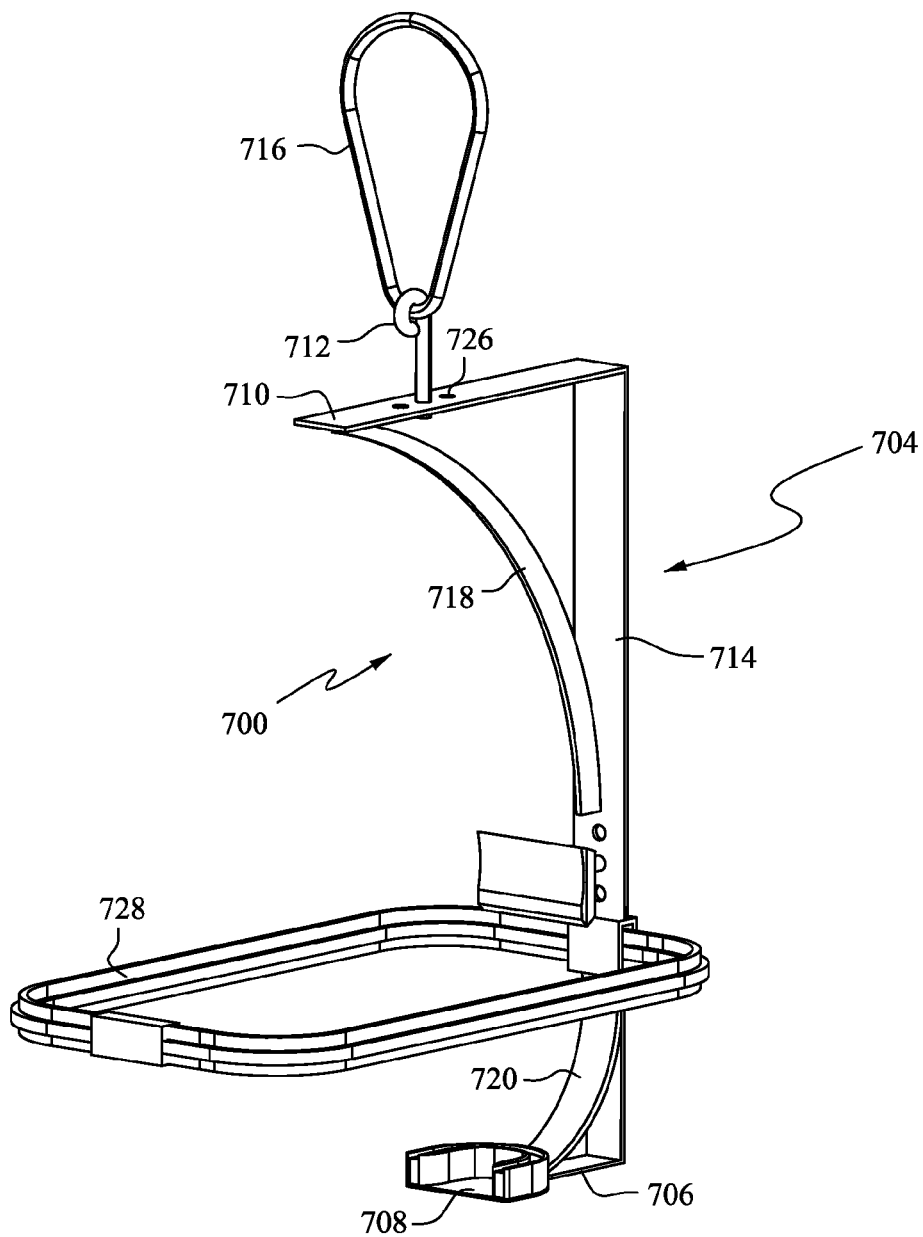
Figure 7E:
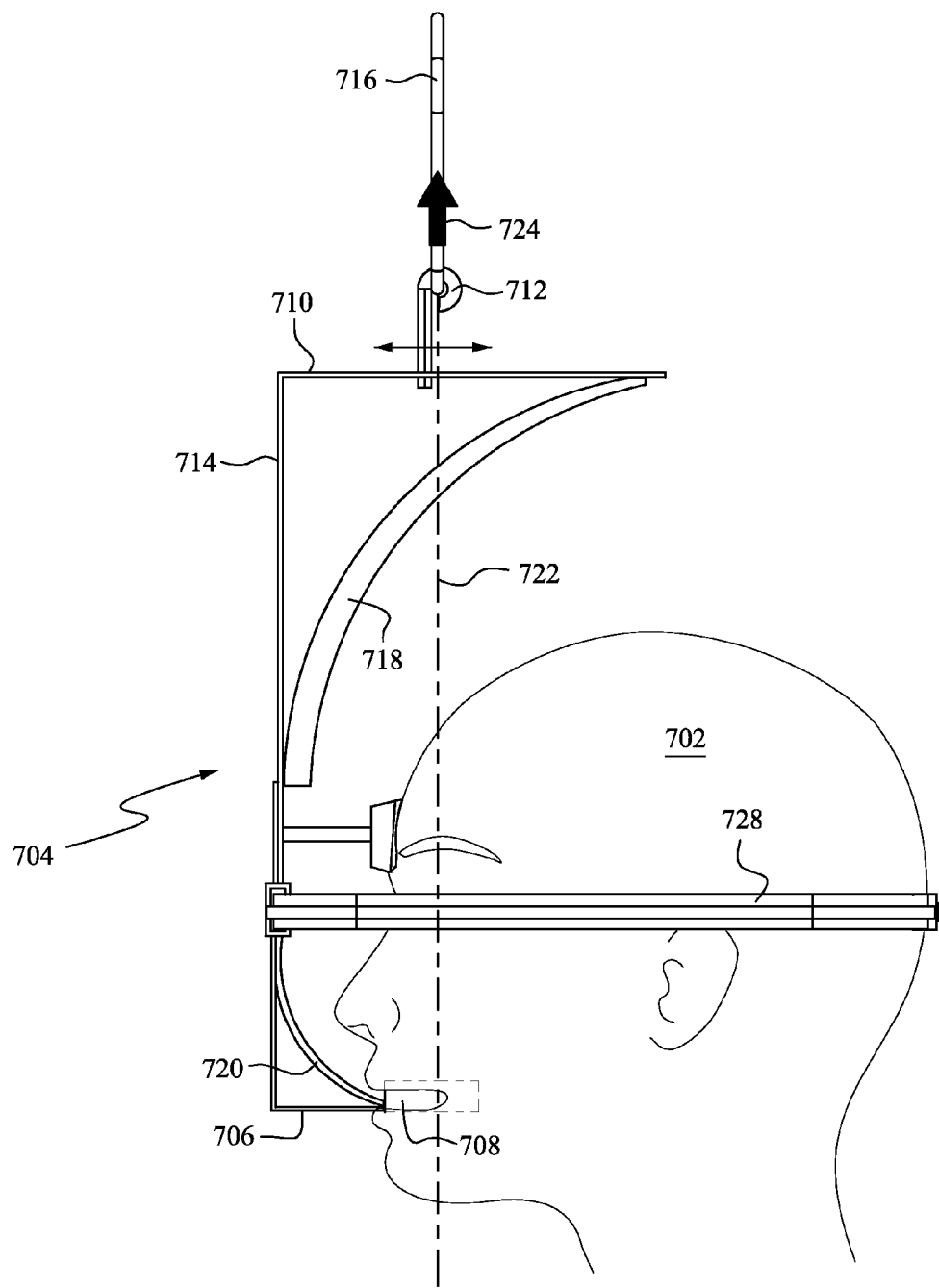

FIG. 6 is a flowchart illustrating the technique for using the apparatus of FIG. 1. Step 601 is to insert the mouth guard into the mouth of the patient. The mouth guard is comfortably positioned inside the mouth of the patient, ensuring a good fit between the mouth guard and at least the upper row of teeth. Step 602 is to adjust the forehead pad to have a good fit with the patient's forehead. To do so, place the forehead pad against the patient's forehead, and adjust the forehead pad assembly such that the backbone 115 of the rigid member 101 is substantially parallel with the plane of the face of the patient. Step 603 is to then adjust the head straps to provide a secure fit. By adjusting the head strap 106, which should be positioned above the ears, the device should be held firmly but comfortably in place. Further adjust optional overhead strap 107 to secure the device in place appropriately. Step 604 is then to apply a tension force to the device via attachment point 102. The tension force should be in the direction of the patient's height, providing long axis spinal decompression.

In additional embodiments of the invention, additional steps may be needed. In an additional embodiment featuring an over-the-door component, an additional step of securing the over-the-door component to a door configured to support appropriate weight precedes the above steps. Additional or substitute steps before or instead of step 604 include manually providing tension force via a rope, cable, or the like configured to pass through the over the door component or activating an automatic tension device utilizing a controller.

In an additional embodiment of the invention featuring a component attached to a rigid wall instead of an over-the-door component, an additional step of securing the device to the wall component, where the wall component is attached to a wall configured to support appropriate weight precedes the above steps. Additional or substitute steps before or instead of step 604 like those discussed above may be necessary.

In an additional embodiment featuring an overhead apparatus not attached to a door or wall, similar steps before and after the steps of FIG. 6 are required to those discussed above. Namely, the device should be attached to such a device featuring an overhead apparatus prior to step 601 and a force is applied manually or automatically before or instead of step 604 as discussed above.

In additional embodiments featuring a patient supporting surface, i.e., a table, an additional step of having a patient lie supine or prone upon the table may be necessary prior to the listed steps. If upper and/or lower extremity immobilization components are utilized, those components likewise would need to be adjusted for fit and comfort prior to fitting the mouth guard to the patient.

FIGS. 7(*a*) to 7(*e*) are illustrations showing various views of a head harness 700. FIG. 7(*a*) is an isonometric view showing in perspective the front and side of the harness. FIG. 7(*b*) is a perspective view of the top and side of the harness. FIG. 7(*c*) is a perspective view of the top and left side of the harness. FIG. 7(*d*) is a perspective view of the top and right side of the harness. And, FIG. 7(*e*) is a side view of the harness when applied to the head 702 of a patient.

The harness 700 includes a C-shaped bracket 704 that is configured to fit in front of and over the face of the patient. The bracket 704 includes a lower leg 706 with a mouth grip 708, an upper leg 710 with a force coupling 712 for a pull force, and a center leg 714 extending between the upper and lower legs.

The center leg may be generally perpendicular, e.g., forming an angle of 80 to 100 degrees, to the lower and upper legs. The bracket may be formed of a metal, such as steel or iron, and is designed to support a pulling load to be applied to the force coupling 712, e.g., a post with an aperture to receive a force coupling device 716.

Support arches 718, 720 may extend between the upper leg and the center leg and the lower leg and the center leg. The support arches increase the rigidity of the C-shaped bracket 704 and suppress the bowing of the center bracket 714 when a force is applied to the force coupling 712. The upper end of the arch 718 is attached to the upper leg 710 at a point distal to the force coupling 712 to suppress bowing of the upper leg. Similarly, the lower end of arch 720 may attached to the lower leg at or near the mouth grip 708 to suppress bowing of the lower leg.

The mouth grip 708 is aligned with the force coupling 712 along a line 722 defined by a force vector 724 applied to the force coupling. The force vector may be coaxial with an axis of the force coupling device 716. The force vector represents the direction and magnitude of force applied to the patient through the harness 700. The force is applied to the patient solely or primarily at the mouth grip 708. Aligning the force vector 724 with the mouth grip 708 allows the harness to transfer the force applied to the coupling 712 entirely or almost entirely, e.g., 80 to 95 percent or more, to the mouth grip. The position of the force coupling 712 may be shifted along the length of the upper leg 710 to effect a desired alignment of the force vector with the mouth grip. The force coupling may be shifted by attaching the coupling to different threaded apertures 726 on the upper leg.

A soft strap 728 is attached to the center leg 714 and is configured to extend around the head 702 of the patient. A pad 730 with a soft covering is attached to the center leg at an elevation slightly higher than the strap. The pad may be adjustable in a vertical direction to align with the forehead of the patient. The strap 728 is slightly tightened to force the pad against the forehead and thereby hold the bracket 700 on the head of the patient. The pad and strap need not be configured to support loads, as their purpose is purely to support or stabilize the position of the mouth guard relative to this device.

This harness 700 may be configured to eliminate or minimize compressive forces applied to the skin of the neck, skull, head, or face. The force applied by the harness is transmitted solely or substantially through the mouth guard to the under surface of the upper teeth and supportive bony structures of the mouth. Other loads applied to the patient, e.g., through the frontal pad or cranial straps, would be uncomfortable to the patient and contrary to the intent of this device.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

I claim:

1. An apparatus for providing skeletal traction comprising:
   a patient supporting device configured to support a weight of a patient and maintain the patient in a predetermined position;
   a head harness further comprising an adjustable rigid member, the rigid member comprising an engagement portion and an attachment point; and
   a force application apparatus, wherein:
   the engagement portion extends into the mouth cavity of a user; the engagement portion further comprises a force application portion, the force application portion is configured to contact at least the upper set of teeth during use;
   the attachment point is located on the rigid member substantially at the same distance from the center of the skull, relative to a body's mid-line, as the center of pressure applied to the user via the force application portion;
   the attachment point is configured to attach to an external force providing apparatus; and
   the attachment point is configured to provide a force in a longitudinal direction via the force application portion; and
   further wherein the attachment point of the head harness is configured to be connected with the patient supporting device such that spinal traction may be applied to a patient during use; and
   the force application apparatus is configured to allow a user to apply a force to the head harness to provide decompression to the patient.

2. The apparatus of claim 1, wherein the patient supporting device provides vibration to the patient during use.

3. The apparatus of claim 1, wherein the patient supporting device provides heat to the patient during use.

4. The apparatus of claim 1, wherein the patient supporting device provides massage to the patient during use.

5. The apparatus of claim 1, wherein the patient supporting device comprises a table.

6. The apparatus of claim 1, wherein the patient supporting device comprises an upper extremity immobilization device.

7. The apparatus of claim 6, wherein the upper extremity immobilization device is configured to provide a shoulder contacting device which prevents movement of a patient's body in the direction of the force applied via the force application device.

8. The apparatus of claim 6, wherein the patient supporting device is configured to provide cervical decompression.

9. The apparatus of claim 7, wherein the patient supporting device is configured to provide cervical decompression.

10. The apparatus of claim 1, wherein the patient supporting device comprises a lower extremity immobilization device.

11. The apparatus of claim 10, wherein the lower extremity immobilization device is configured to provide a lower extremity contacting device which prevents movement of a patient's body in the direction of the force applied via the force application device.

12. The apparatus of claim 10, wherein the patient supporting device is configured to provide lumbar decompression.

13. The apparatus of claim 11, wherein the patient supporting device is configured to provide lumbar decompression.

14. The apparatus of claim 1, wherein the force application apparatus further comprises a controller.

15. The apparatus of claim 14, wherein the controller is configured to execute at least a stored program which provides a force to the head harness.

16. The apparatus of claim 15, wherein the controller is configured to provide an automatically adjusting force configured to provide a patient-specific decompression treatment via the force application apparatus.

17. A method of providing skeletal traction comprising:
    inserting a force application portion attached to an engagement portion of an adjustable rigid member into the mouth of a user, the force application portion being configured to contact at least the upper set of teeth during use;
    applying a force via at least the force application portion whose vector is directed in a longitudinal direction, the force being adapted to supply tension forces to the user during use;
    wherein the force is applied via an external force providing apparatus which is connected to the engagement portion via an attachment point on a rigid member, the attachment point being located substantially at the same distance from the center of the skull, relative to a body's mid-line, as the center of pressure applied to the user via the force application portion.

18. The method of claim 17, wherein the patient is positioned on a patient support device prior to the application of force.

19. The method of claim 18, wherein the patient support device is configured to provide skeletal decompression.

20. The method of claim 18, wherein the patient support device is configured to provide cervical decompression.

21. The method of claim 18, wherein the patient support device is configured to provide lumbar decompression.

22. The method of claim 19, wherein the patient supporting device comprises an upper extremity immobilization device.

23. The apparatus of claim 22, wherein the upper extremity immobilization device is configured to provide a shoulder contacting device which prevents movement of a patient's body in the direction of the force applied via the force application device.

24. The method of claim 19, wherein the patient supporting device comprises a lower extremity immobilization device.

25. The method of claim 24, wherein the lower extremity immobilization device is configured to provide a lower extremity contacting device which prevents movement of a patient's body in the direction of the force applied via the force application device.

26. The method of claim 17, wherein the force application apparatus further comprises a controller.

27. The apparatus of claim 26, wherein the controller is configured to execute at least a stored program which provides a force to the head harness.

28. The apparatus of claim 26, wherein the controller is configured to provide an automatically adjusting force configured to provide a patient-specific decompression treatment via the force application apparatus.

* * * * *